United States Patent
Kitamura

(10) Patent No.: US 11,457,917 B2
(45) Date of Patent: Oct. 4, 2022

(54) TREATMENT INSTRUMENT

(71) Applicant: Olympus Corporation, Hachioji (JP)

(72) Inventor: Ojiro Kitamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 245 days.

(21) Appl. No.: 16/693,535

(22) Filed: Nov. 25, 2019

(65) Prior Publication Data

US 2020/0093491 A1    Mar. 26, 2020

Related U.S. Application Data

(63) Continuation of application No. PCT/JP2017/021513, filed on Jun. 9, 2017.

(51) Int. Cl.
*A61B 17/072* (2006.01)
*A61B 17/068* (2006.01)
*A61B 34/30* (2016.01)
*A61B 17/00* (2006.01)
*A61B 17/29* (2006.01)

(52) U.S. Cl.
CPC .... *A61B 17/07207* (2013.01); *A61B 17/0682* (2013.01); *A61B 34/30* (2016.02); *A61B 2017/00398* (2013.01); *A61B 2017/00477* (2013.01); *A61B 2017/07221* (2013.01); *A61B 2017/2927* (2013.01)

(58) Field of Classification Search
CPC .......... A61B 17/07207; A61B 17/0682; A61B 2017/07221; A61B 17/068
USPC ...................................................... 227/175.1
See application file for complete search history.

(56) References Cited

U.S. PATENT DOCUMENTS 5,485,952 A * 1/1996 Fontayne ......... A61B 17/07207
227/111
5,649,955 A   7/1997 Hashimoto et al.
(Continued)

FOREIGN PATENT DOCUMENTS

JP   H07-255734 A   10/1995
JP   H11-313834 A   11/1999
(Continued)

OTHER PUBLICATIONS

Aug. 8, 2017 International Search Report issued in International Application No. PCT/JP2017/021513.
(Continued)

*Primary Examiner* — Michelle Lopez
(74) *Attorney, Agent, or Firm* — Oliff PLC

(57) ABSTRACT

The disclosed technology is directed to a treatment instrument comprises an end effector having a pair of clamping members configured to pivot with respect to one another. A sheath is attached to the end effector along a longitudinal axis so that the end effector can be bent or curved. A drive shaft is connected to the end effector so as to guide the end effector to open or close the pair of clamping members relative to one another when moved in a longitudinal direction relative to the sheath. An elongated member is connected to the end effector and is configured to make the end effector bend or curve with respect to the sheath when moved in the longitudinal direction relative to the sheath. First and second members are configured to produce first and second forces sufficient to open or close the pair of clamping members.

9 Claims, 6 Drawing Sheets

(56) References Cited

U.S. PATENT DOCUMENTS

| | | | |
|---|---|---|---|
| 5,762,256 A * | 6/1998 | Mastri | A61B 17/0684 227/176.1 |
| 5,820,009 A * | 10/1998 | Melling | A61B 17/07207 227/176.1 |
| 7,954,685 B2 * | 6/2011 | Viola | A61B 17/105 227/19 |
| 2012/0130420 A1 | 5/2012 | Nicholas et al. | |
| 2014/0135762 A1 | 5/2014 | Masuda et al. | |
| 2015/0066022 A1 | 3/2015 | Shelton, IV et al. | |

FOREIGN PATENT DOCUMENTS

| | | |
|---|---|---|
| JP | 2012-110675 A | 6/2012 |
| JP | 2013-042921 A | 3/2013 |
| WO | 2013/141217 A1 | 9/2013 |

OTHER PUBLICATIONS

Dec. 10, 2019 International Preliminary Report on Patentability issued in International Application No. PCT/JP2017/021513.

* cited by examiner

TREATMENT INSTRUMENT

CROSS-REFERENCE TO RELATED APPLICATION

This application is a continuation application of PCT Application No. PCT/JP 2017/021513 filed on Jun. 9, 2017, which is hereby incorporated by reference in its entirety.

TECHNICAL FIELD

The disclosed technology relates to a treatment instrument that can grasp a treatment target such as a biological tissue between a pair of clamping members included in an end effector.

DESCRIPTION OF THE RELATED ART

US Patent Application 2015/0066022 A1 discloses a treatment instrument that can grasp a treatment target, such as a body tissue, between a pair of clamping members included in an end effector. In this treatment instrument, the end effector can be bent or curved with respect to a sheath disposed extending along a straight longitudinal axis. Further, a drive shaft is moved in the direction of its axis by control or the like through a grip handle in this treatment instrument. As a result, the clamping members are closed relative to each other so that the treatment target can be grasped between the clamping members. Here, the amount of grasping force between the clamping members changes corresponding to an axial force that is applied from the drive shaft to the end effector.

In a state in which the end effector is bent or curved, the axial force of the drive shaft, which affects the amount of grasping force between the pair of clamping members, tends to decrease compared with that in a neutral state that the end effector is disposed extending straight relative to the sheath. In the state in which the end effector is bent or curved, the amount of grasping force between the clamping members therefore tends to decrease compared with that in the neutral position. Among many, there is a desire to make the axial force of the drive shaft, in other words, the amount of grasping force between the clamping members uniform or substantially uniform, for example, at any angle of bending of the end effector upon performing treatment while gasping a treatment target between the clamping members. A demand has thus arisen to control the axial force of the drive shaft, in other words, the amount of grasping force between the clamping members to a level suited for treatment corresponding to the position of bending or curving of the end effector.

Brief Summary of Embodiments

The disclosed technology has been made in view of the foregoing.

One aspect of the disclosed technology is directed to a treatment instrument comprises an end effector having a pair of clamping members configured to pivot with respect to one another so as to be in an open or close position. A sheath is attached to the end effector along a longitudinal axis so that the end effector can be bent or curved. A drive shaft is connected to the end effector so as to guide the end effector to open or close the pair of clamping members relative to one another when moved in a longitudinal direction relative to the sheath. An elongated member is connected to the end effector and is configured to make the end effector bend or curve with respect to the sheath when moved in the longitudinal direction relative to the sheath. A first member is configured to produce a first force sufficient to open or close the pair of clamping members and to apply the first force to the drive shaft. A second member is configured to produce a second force that corresponds to a degree of bending or curving of the end effector and to apply the second force to the drive shaft.

Another aspect of the disclosed technology is directed to a treatment instrument comprises a housing and a sheath is attached to the housing along a longitudinal axis. An end effector is configured to be attached to the sheath so as to be bend or curved with respect to the sheath. The end effector includes a pair of clamping members configured to pivot with respect to one another so as to be in an open or close position. A drive shaft is configured to be disposed inside the sheath and is connected to the end effector so as to guide the end effector to open or close the pair of clamping members relative to one another when moved in a longitudinal direction relative to the sheath. An elongated member is connected to the end effector and is configured to make the end effector bend or curve with respect to the sheath when moved in the longitudinal direction relative to the sheath. A first member is configured to produce a first force sufficient to open or close the pair of clamping members and to apply the first force to the drive shaft. A second member is configured to produce a second force that corresponds to a degree of bending or curving of the end effector and to apply the second force to the drive shaft.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The disclosed technology has as an object thereof the provision of a treatment instrument that can control the amount of grasping force between clamping members to a desired level corresponding to the position of bending or curving.

First Embodiment

Regarding a first embodiment of the present invention, a description will be made with reference to FIGS. 1 to 8.

Figure 1:
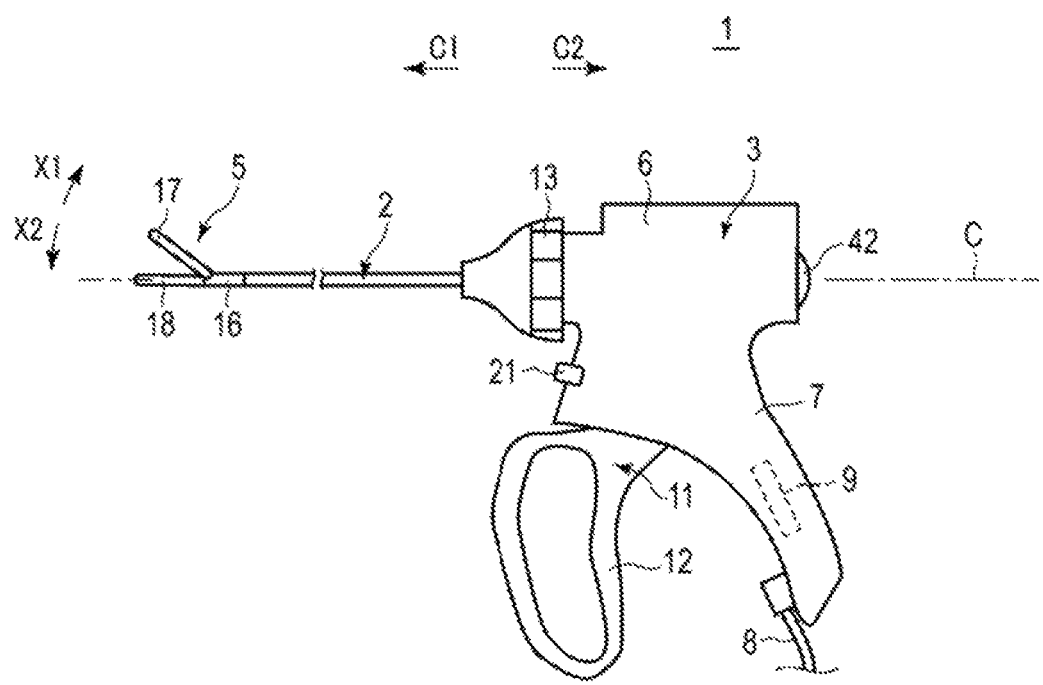
FIG. 1 is a schematic view illustrating a configuration of a treatment instrument according to a first embodiment.

FIG. 1 is a view illustrating a configuration of a treatment instrument 1 of this embodiment. As illustrated in FIG. 1, the treatment instrument 1 includes a tubular sheath 2, a hand-holdable housing 3, and an end effector 5. The sheath 2 has a straight or substantially straight, longitudinal axis C as a central axis. Now, one side in a direction along the longitudinal axis C is referred to as the distal end side, or the side of arrow C1, and a side opposite to the distal end side is referred to as the proximal end side, or the side of arrow C2. The sheath 2 is disposed extending from the proximal end side toward the distal end side along the longitudinal axis C, and the housing 3 is connected to a proximal end side of the sheath 2.

The housing 3 includes a housing main body 6 and a grip 7, or stationary grip handle. The housing main body 6 is disposed extending along the longitudinal axis C. The grip 7, or stationary grip handle is disposed extending from the housing main body 6 in a direction intersecting the longitudinal axis C. The grip 7 is disposed at a location apart from the longitudinal axis C. A cable 8 is connected at an end thereof to the grip 7. The cable 8 is connected at an opposite end thereof to an unillustrated power-source device or control device. The power-source device can supply electrical energy to the treatment instrument 1 via unillustrated electrical wiring or the like disposed extending inside the cable 8.

A grip handle 11, or movable grip handle is pivotally attached to the housing 3. When the grip handle 11 is pivotally moved relative to the housing 3, the grip handle 11 opens or closes relative to the grip 7. Further, a stopper 9 is disposed inside the grip 7. In a state in which the grip handle 11 is most closed toward the grip 7, the grip handle 11 is in contact with the stopper 9. The grip handle 11 includes an operating-force applied portion 12, to which an operating force is applied to open or close the grip handle 11 relative to the grip 7. An operation to open or close the grip handle 11 relative to the grip 7 is inputted through the operating-force applied portion 12.

In this embodiment, the treatment instrument 1 has a handgun shape, and the operating-force applied portion 12 is located on a side, where the grip 7 is located, with respect to the longitudinal axis C and on the distal end side relative to the grip 7. Upon opening or closing the grip handle 11 relative to the grip 7, the moving direction of the grip handle 11 is substantially parallel to the longitudinal axis C. In an example, the grip handle 11 is located on the proximal end side with respect to the grip 7. In another example, the operating-force applied portion 12 is located on a side opposite to the side, where the grip 7 is located, with respect to the longitudinal axis C, and upon opening or closing the grip handle 11 relative to the grip 7, the moving direction of the grip handle 11 intersects or is substantially perpendicular to the longitudinal axis C.

In this embodiment, a rotary knob 13 is also attached as an operating member to the housing 3. The sheath 2 is fixed to the rotary knob 13, and is inserted from the distal end side into the rotary knob 13. When the rotary knob 13 is rotated, the sheath 2 rotates together with the rotary knob 13 about the longitudinal axis C relative to the housing 3. In an example, the rotary knob 13 may be omitted, and the sheath 2 may be non-rotatable about the longitudinal axis C relative to the housing 3.

Figure 2:
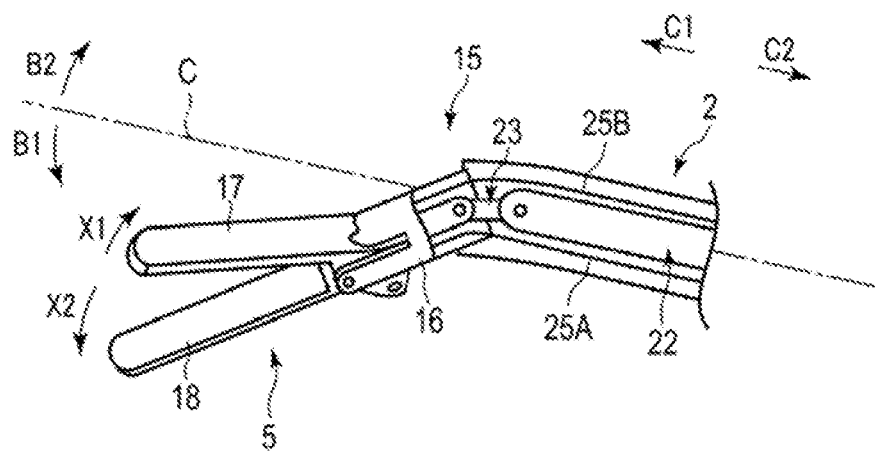
FIG. 2 is a schematic view illustrating an example of a configuration of a distal end portion of a sheath and an end effector in the first embodiment.

FIG. 2 is a view illustrating an example of a configuration of a distal end portion of the sheath 2 and the end effector 5. In this embodiment, the end effector 5 is attached to the distal end portion of the sheath 2. The end effector 5 can be bent or curved with respect to the sheath 2 or the longitudinal axis C. In the example of FIG. 2, an articulated joint 15 is formed between the sheath 2 and the end effector 5 so that the end effector 5 is bendable with respect to the sheath 2. A bending direction of the end effector 5, specifically a direction indicated by arrows B1 and B2 intersects or is substantially perpendicular to the longitudinal axis C. In the example in which the rotary knob 13 is disposed, the end effector 5 is rotatable together with the sheath 2 and rotary knob 13 relative to the housing 3 about the longitudinal axis C. In an example, a bendable tube (not illustrated) is disposed between the end effector 5 and the sheath 2 instead of the formation of the articulated joint 15. The bendable tube is formed from a plurality of bending elements (not illustrated), which are each pivotally connected to the adjacent bending elements.

The end effector 5 includes an effector main body 16, a first clamping member 17, or first grasping jaw, and a second clamping member 18, or second grasping jaw. The effector main body 16 is attached to the distal end portion of the sheath 2 so that the effector main body 16 can be bent or curved with respect to the sheath 2. In the end effector 5, the pair of clamping members 17 and 18 can be opened or closed relative to one another. An operating direction of the pair of clamping members 17 and 18 upon relative opening or closure of the clamping members 17 and 18, specifically a direction indicated by arrows X1 and X2 intersects or is substantially perpendicular to the longitudinal axis C, and also intersects or is substantially perpendicular to the bending direction or curving direction of the end effector 5. When closed relative to each other, the clamping members 17 and 18 can grasp a treatment target, such as a body tissue, between them.

Now, in an example, one of the clamping members 17 and 18 is integrated with the effector main body 16 or is fixed to the effector main body 16, and the other one is pivotally attached to the effector main body 16. In another example, the clamping member 17 and 18 are both pivotally attached to the effector main body 16. In a further example, a rod member (not illustrated) is disposed extending from an inside of the effector main body 16 toward the distal end side, and one of the clamping members 17 and 18 is formed by a portion of the rod member, the portion extending toward the distal end side from the effector main body 16. On the other hand, the other one of the clamping members 17 and 18 is pivotally attached to the effector main body 16.

In addition, an operation button 21 is attached as an operating member to the housing 3. Through the operation button 21, an operation is inputted to supply electrical energy from the power-source device to the treatment instrument 1. In an example, when an operation is inputted through the operation button 21 and electrical energy is supplied to the treatment instrument 1, any one of high-frequency current, ultrasonic vibrations and heat from a heater is applied as treatment energy to the treatment target grasped between the clamping members 17 and 18, for example, as in known treatment instruments. In another example, when an operation is inputted through the operation button 21 and electrical energy is supplied to the treatment instrument 1, an electric motor is driven, and a staple is driven through the treatment target grasped between the clamping members 17 and 18. In a further example, instead of or in addition to the operation button 21, a footswitch or the like which is discrete from the treatment instrument 1 is disposed as an operating member through which an operation is inputted to supply electrical energy from the power-source device to the treatment instrument 1.

In this embodiment, a drive shaft 22 is disposed extending along the longitudinal axis C inside the sheath 2. The drive shaft 22 is movable relative to the sheath 2 along an axial direction of the drive shaft 22 or the longitudinal axis C. The drive shaft 22 is connected at a distal end or an end thereof to the end effector 5. The drive shaft 22 is inserted from the distal end side into the housing 3, and is connected at a proximal end portion thereof to the grip handle 11 inside the housing main body 6 or inside the housing 3. When the drive shaft 22 is moved relative to the sheath 2 along the axial direction of the drive shaft 22 or the longitudinal axis C, the clamping members 17 and 18 open or close relative to each other. In the example in which the rotary knob 13 is disposed, the drive shaft 22 rotates together with the sheath 2 and end effector 5 about the longitudinal axis C when the rotary knob 13 is rotated.

In the example illustrated in FIG. 2, a link mechanism 23 is disposed on the drive shaft 22 at a state in which the drive shaft 22 passes through the articulated joint 15. Described specifically, the link mechanism 23 is disposed on the drive shaft 22 at a state in which the drive shaft 22 passes between the end effector 5 and the sheath 2. Owing to the disposition of the link mechanism 23, the drive shaft 22 is bent or curved at a position thereof, which is on the distal end side relative to the link mechanism 23, with respect to the sheath 2 or the longitudinal axis C, corresponding to bending or curving of the end effector 5, even if the end effector 5 is bent or curved with respect to the sheath 2. In short, the drive shaft 22 is bent or curved at a distal end portion thereof corresponding to bending or curving of the end effector 5. In an example, a leaf spring or a rope is disposed instead of the link mechanism 23 on the drive shaft 22 at the position where the drive shaft 22 passes between the end effector 5 and the sheath 2. In this case, the distal end portion of the drive shaft 22 is also bent or curved corresponding to bending or curving of the end effector 5.

A pair of elongated members 25A and 25B is also disposed extending along the longitudinal axis C inside the sheath 2. The elongated members 25A and 25B are each formed from any one of a wire member, a leaf spring member and a bar member, or are each formed by combining plural ones of these members. The elongated members 25A and 25B are each movable along an axial direction or the longitudinal axis C relative to the sheath 2. The elongated members 25A and 25B are each connected at a distal end or one end thereof to the end effector 5. Further, the elongated members 25A and 25B are inserted from the distal end side into the housing 3 or into the housing main body 6. When the elongated members 25A and 25B are moved along the axial direction or the longitudinal axis C relative to the sheath 2, the end effector 5 is bent or curved with respect to the sheath 2.

In the example in which the rotary knob 13 is disposed, the elongated members 25A and 25B rotate together with the sheath 2, end effector 5 and drive shaft 22 about the longitudinal axis C when the rotary knob 13 is rotated. The elongated members 25A and 25B each have flexibility, and the elongated members 25A and 25B are each bent or curved at a distal end portion thereof corresponding to bending or curving of the end effector 5.

FIGS. 3 to 8 are views illustrating an internal configuration of the housing 3. As illustrated in FIGS. 3 to 8, the grip handle 11 is pivotally attached to the housing 3 via a fulcrum pin 26. Therefore, the fulcrum pin 26 has a central axis, which is used as a pivot P1, or pivot center of the grip handle 11. In this embodiment, the pivot P1 is disposed extending along a width direction of the housing 3.

The drive shaft 22 includes a rod member 31, a transmission member 32, and a cylinder member 33. The rod member 31 is disposed extending from an inside of the housing 3 and through an inside of the sheath 2, and is connected at a proximal end thereof to the transmission member 32. The cylinder member 33 is attached from the proximal end side to the transmission member 32. As the drive shaft 22, the rod member 31, transmission member 32 and cylinder member 33 move together along the longitudinal axis C relative to the sheath 2 and housing 3. In the example of FIG. 2, for example, the rod member 31 is connected at a distal end thereof to the link mechanism 23 of the drive shaft 22. The transmission member 32 and cylinder member 33 are arranged inside the housing main body 6. The cylinder member has a central axis, which is disposed coaxially or substantially coaxially with the longitudinal axis C of the sheath 2. The cylinder member 33 is disposed extending from the transmission member 32 toward the proximal end side. In this embodiment, the cylinder member 33 is arranged between the fulcrum pin 26 or pivot P1 and the operating-force applied portion 12 of the grip handle 11.

A cylindrical slider 35, or first slider and a cylindrical elastic member 36, or first elastic member such as a coil spring are accommodated inside the housing 3. The slider 35 is disposed on an outer circumferential surface of the cylinder member 33 of the drive shaft 22. The slider 35 is movable along the longitudinal axis C relative to the drive shaft 22. However, a restriction is placed on rotation of the slider 35 about the longitudinal axis C relative to the drive shaft 22. In the example in which the rotary knob 13 is disposed, the slider 35 therefore rotates together with the drive shaft 22 and rotary knob 13 about the longitudinal axis C relative to the housing 3 when the rotary knob 13 is rotated. On an outer circumferential portion of the cylinder member 33, a stopper 37 is also formed. The stopper 37 is disposed on the distal end side relative to the slider 35, and is fixed to the cylinder member 33 of the drive shaft 22. When the slider 35 comes into contact with the stopper 37, movement of the slider 35 beyond the stopper 37 to a region on the distal end side is restricted.

In this embodiment, a flange 38 is formed on the outer circumferential surface of the cylinder member 33, and the flange 38 extends radially outward. The flange 38 is formed, for example, integrally with the cylinder member 33, and is disposed on the proximal end side relative to the slider 35. In an outer circumferential surface of the slider 35, a groove 41 is disposed extending about the longitudinal axis C. The groove 41 is recessed radially inward. In this embodiment, the groove 41 is formed over the entire circumference about the longitudinal axis C. The grip handle 11 is attached to the slider 35 through its engagement with the slider 35 at the groove 41. In this embodiment, the grip handle 11 has an engagement portion disposed between the fulcrum pin 26 or pivot P1 and the operating-force applied portion 12. The engagement portion is maintained in engagement with the slider 35.

The elastic member 36 is disposed on the outer circumferential surface of the cylinder member 33 of the drive shaft 22, and can apply an restoring force, i.e., a first restoring force to the drive shaft 22. The elastic member 36 is disposed extending along the longitudinal axis C between the flange 38 and the slider 35. The elastic member 36 is in contact or connected at an end or a proximal end thereof with or to the flange 38. On the other hand, the elastic member 36 is in contact or connected at an opposite end or a distal end thereof with or to the slider 35. When the slider 35, or first slider is moved along the longitudinal axis C relative to the drive shaft 22, the elastic member 36 is extended or compressed.

In this embodiment, in a state that the slider 35 is in contact with the stopper 37, in other words, also in a state that the slider 35 is most remote from the flange 38, the elastic member 36, or first elastic member is in a state of having been compressed from a natural length. Even in the state that the slider 35 is in contact with the stopper 37, the restoring force or first restoring force is applied toward the distal end side from the elastic member 36 to the drive shaft 22. When the slider 35 moves toward the proximal end side relative to the drive shaft 22 from the state that the slider 35 is in contact with the stopper 37, the elastic member 36 is compressed further so that the restoring force or first restoring force from the elastic member 36 to the drive shaft 22 increases.

Upon grasping the treatment target between the clamping members 17 and 18, the treatment target is arranged between the clamping member 17 and 18 with the grip handle 11 widely opened relative to the grip 7, and the grip handle 11 is then closed toward the grip 7. As a consequence, the grip handle 11 presses the slider 35 toward the proximal end side, and a pressing force is transmitted to the drive shaft 22 via the elastic member 36, whereby the drive shaft 22 moves together with the slider 35 and elastic member 36 toward the proximal end side relative to the sheath 2. In this embodiment, when the drive shaft 22 is moved toward the proximal end side, at least one of the clamping members 17 and 18 pivots relative to the effector main body 16 so that the clamping members 17 and 18 are closed relative to each other. Here, the clamping member 17 or 18, or the clamping members 17 and 18 pivots or pivot until the treatment target is compressed to a certain extent, so that the clamping members 17 and 18 are closed relative to each other until the treatment target is compressed to the certain extent.

When the grasped treatment target is compressed to the certain extent, the pivotal movement of the clamping member 17 or 18, or the clamping members 17 and 18 stops, and the movement of the drive shaft 22 toward the proximal end side also stops. When the grip handle 11 is closed toward the grip 7 in this state until the grip handle 11 comes into contact with the stopper 9, a pressing force from the grip handle 11 is transmitted to the slider 35 so that the slider 35, or first slider moves toward the distal end side relative to the drive shaft 22. As a consequence, the elastic member 36 or first elastic member compresses, and the restoring force or first restoring force applied toward the proximal end side from the elastic member 36 to the drive shaft 22 increases. By the increase of the restoring force from the elastic member 36 to the drive shaft 22, the axial force applied toward the proximal end side from the drive shaft 22 to the end effector 5 increases so that the amount of grasping force on the treatment target between the clamping members 17 and 18 increases.

Figure 3:
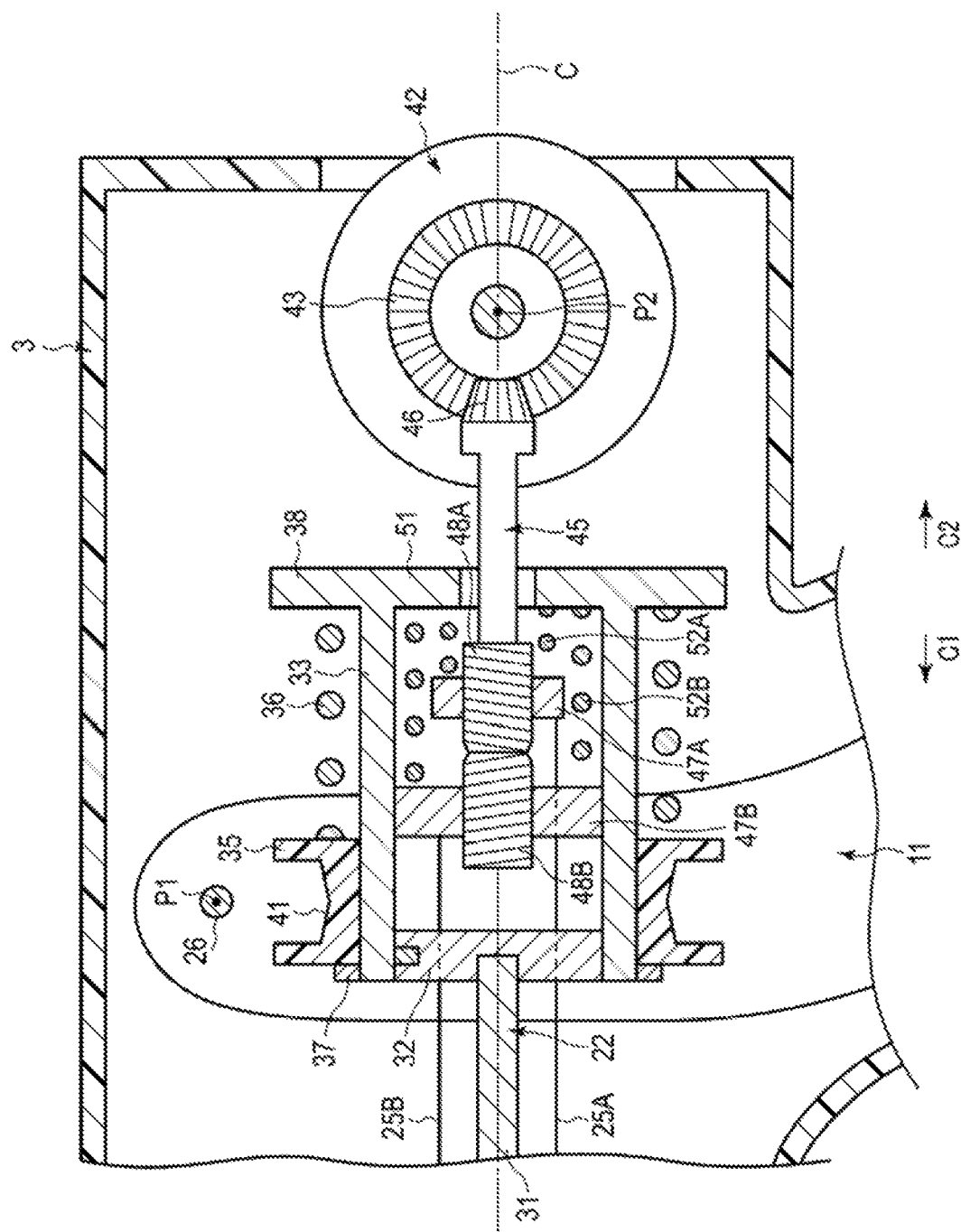
FIG. 3 is a schematic view illustrating an internal configuration of a housing in the first embodiment, with the end effector being in a neutral state and clamping members being in a state in which the clamping members are widely opened relative to one another.
Figure 4:
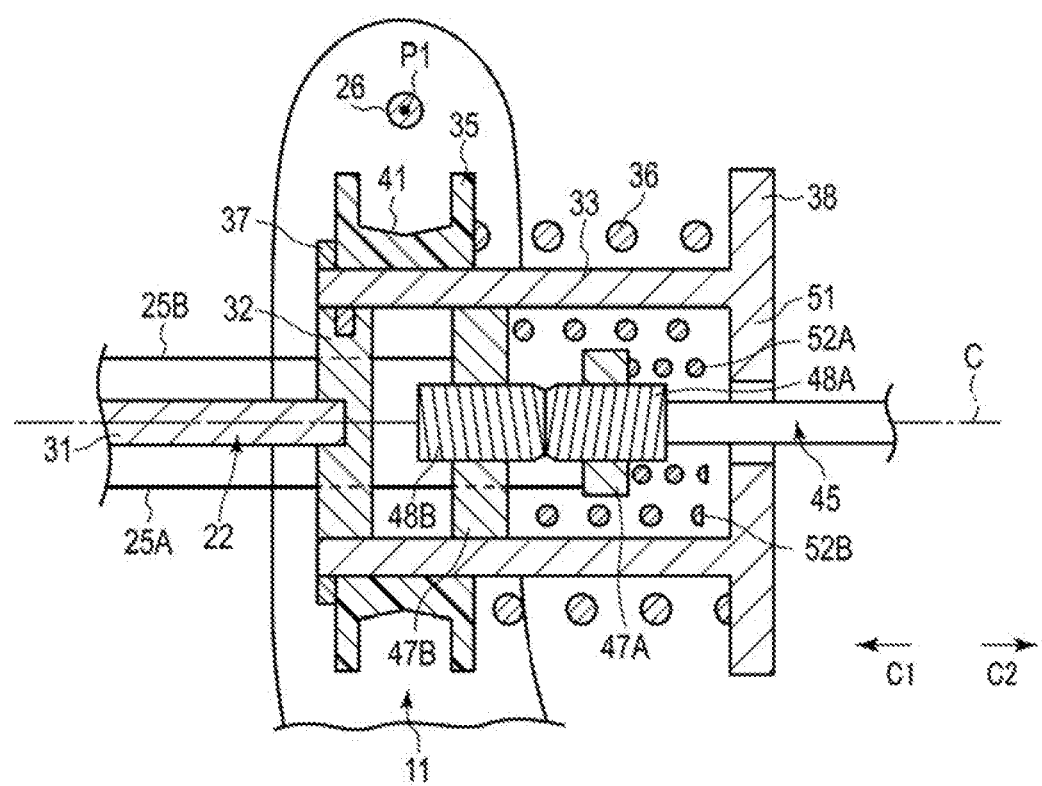
FIG. 4 is a schematic view illustrating the internal configuration of the housing in the first embodiment, with the end effector being in the neutral position and a drive shaft being in a state in which movement of the drive shaft toward a proximal end side has stopped.
Figure 5:
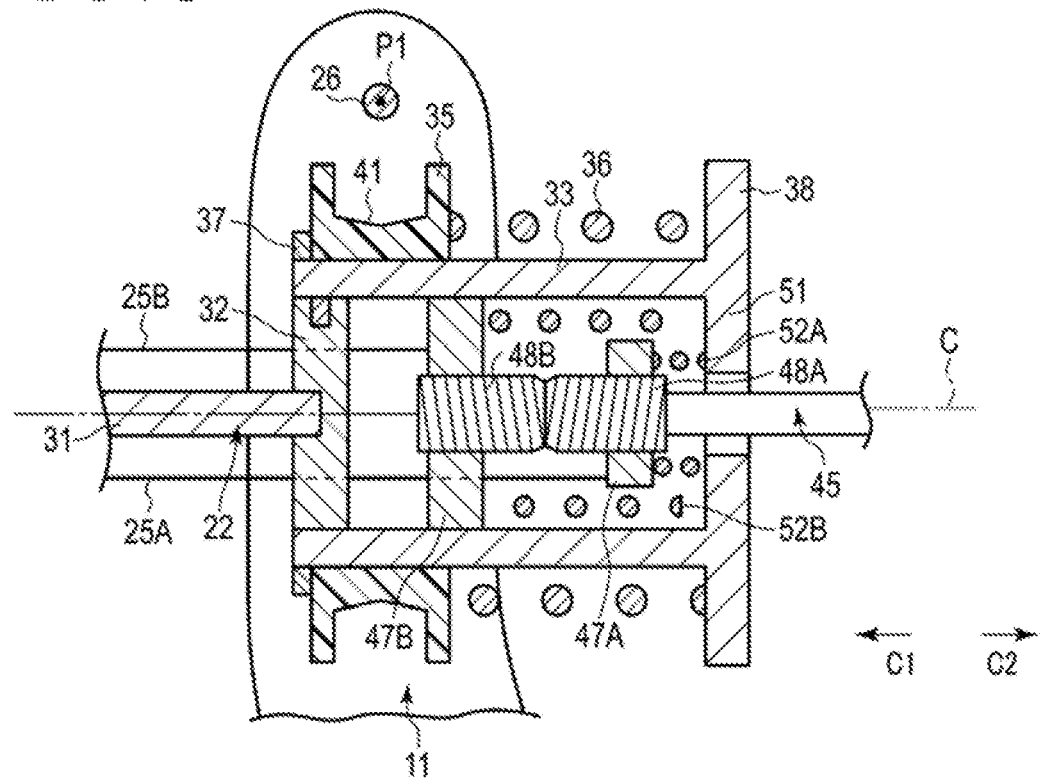
FIG. 5 is a schematic view illustrating the internal configuration of the housing in the first embodiment, with the end effector being in a state in which the end effector is bent toward one side in bending direction and the clamping members being in the state in which the clamping members are widely opened relative to one another.
Figure 6:
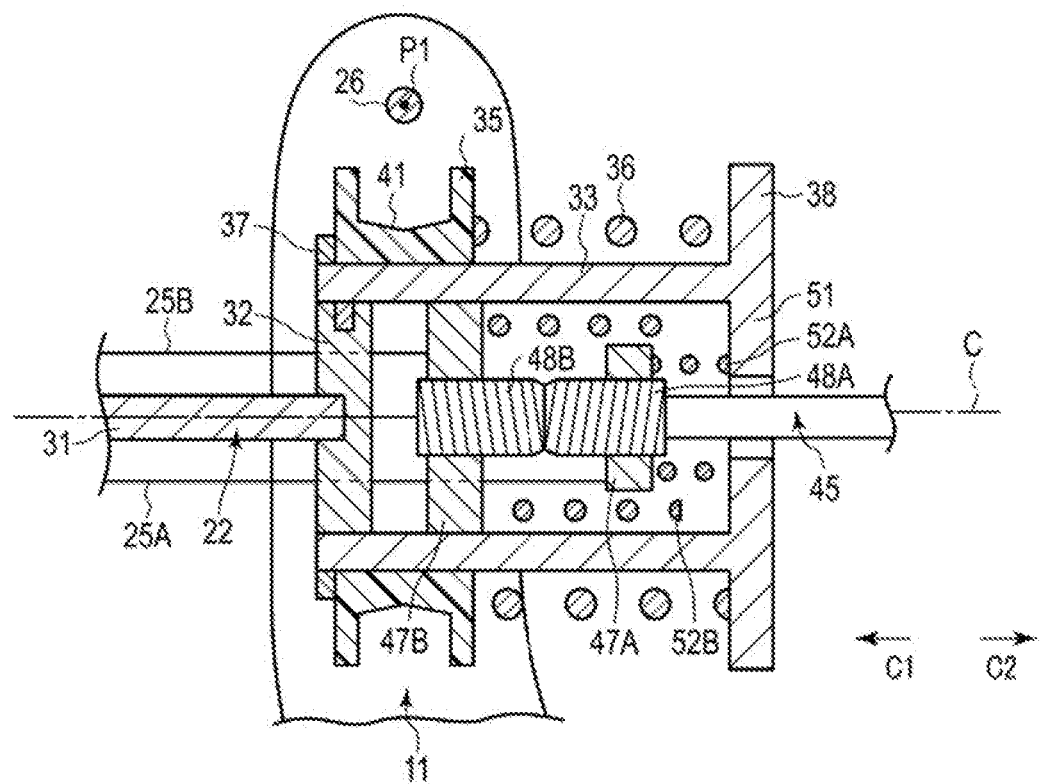
FIG. 6 is a schematic view illustrating the internal configuration of the housing in the first embodiment, with the end effector being in the state in which the end effector is bent toward the one side in bending direction and the drive shaft being in a state in which movement of the drive shaft toward the proximal end side has stopped.
Figure 7:
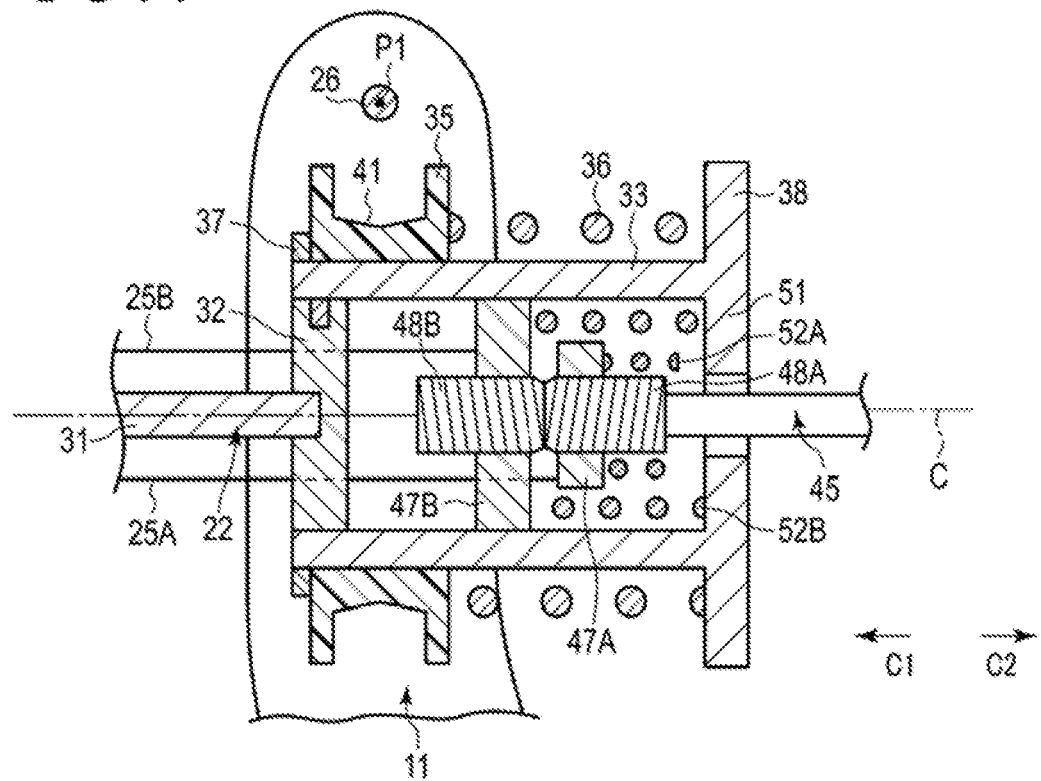
FIG. 7 is a schematic view illustrating the internal configuration of the housing in the first embodiment, with the end effector being in a state in which the end effector is bent to a side opposite to the side in FIGS. 5 and 6, and the clamping members being in the state in which the clamping members are widely opened relative to one another.
Figure 8:
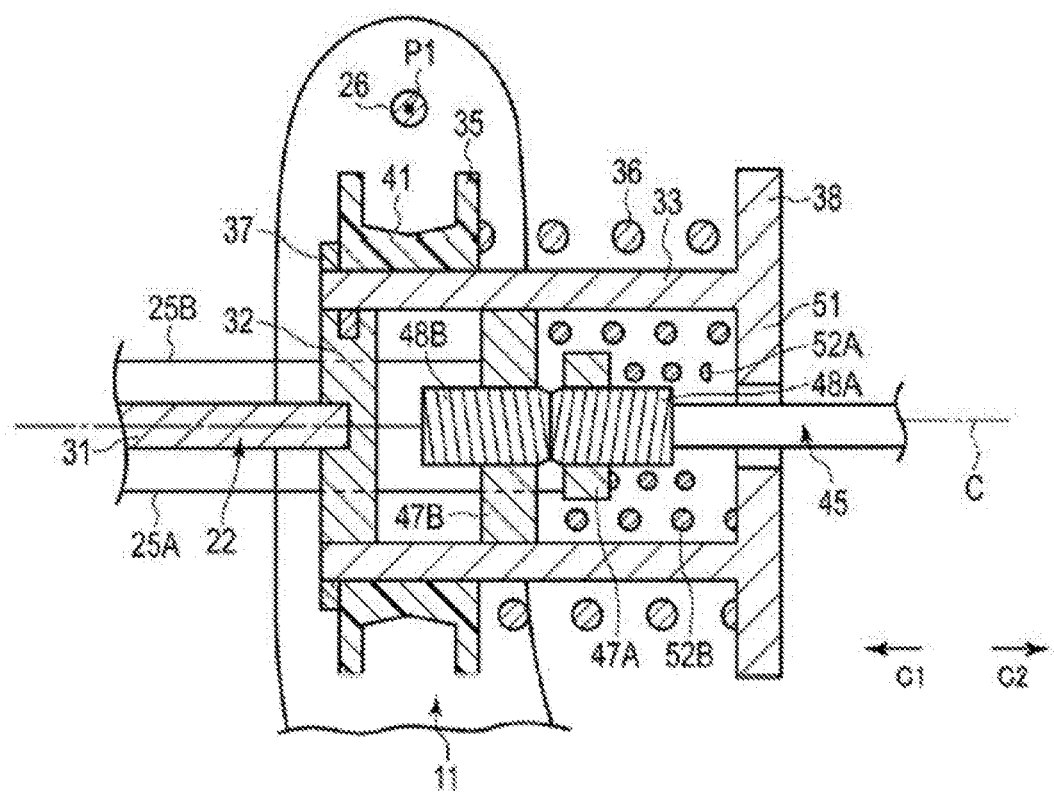
FIG. 8 is a schematic view illustrating the internal configuration of the housing in the first embodiment, with the end effector being in the state in which the end effector is bent toward the side opposite to the side in FIGS. 5 and 6, and the drive shaft being in the state in which movement of the drive shaft toward the proximal end side has stopped.

FIGS. 3, 5 and 7 illustrate the internal configuration of the housing 3 with the clamping members 17 and 18 being in a state in which the clamping members 17 and 18 are most opened relative to each other. On the other hand, FIGS. 4, 6 and 8 illustrate the internal configuration of the housing 3 in a state in which the treatment target grasped by closure of the clamping members 17 and 18 relative to each other has been compressed to the certain extent and the movement of the drive shaft 22 toward the proximal end side has stopped.

In the treatment instrument 1, a control dial 42 is also disposed as a control member through which an operation to bend or curve the end effector 5 is inputted. The control dial 42 is rotatable about an axis P2 of rotation relative to the housing 3. The axis P2 of rotation is disposed extending along a direction that intersects the longitudinal axis C. In the example of FIG. 1, the control dial 42 is arranged through a proximal end side of the housing main body 6. On the control dial 42, a gear portion 43 is formed about the axis P2 of rotation. In this embodiment, the gear portion 43 is formed over the entire circumference about the axis P2 of rotation. In an example, the gear portion 43 may be disposed in only a part of a range about the axis P2 of rotation. Further, the gear portion 43 is arranged inside the housing 3, and is not exposed to an outside of the housing 3. In FIGS. 4 to 8, the housing 3 and control dial 42 are omitted.

A rotary shaft 45 is also disposed inside the housing 3. In this embodiment, the rotary shaft 45 is inserted from the proximal side into the cylinder member 33 of the drive shaft 22. A gear portion 46 is formed on a proximal end portion of the rotary shaft 45. The gear portion 46 is in meshing engagement with the gear portion 43 of the control dial 42. When the control dial 42 rotates about the axis P2 of rotation by a control through the control dial 42, the rotary shaft 45 rotates about a central axis of the rotary shaft 45. In this embodiment, the central axis of the rotary shaft 45 is parallel or substantially parallel to the longitudinal axis C.

Sliders 47A and 47B are attached to the rotary shaft 45. The sliders 47A and 47B are each, for example, a ring-shaped nut. In the example of FIGS. 3 to 8, the slider 47A is located on the proximal end side with respect to the slider 47B. On an outer circumferential surface of the rotary shaft 45, threaded portions 48A and 48B are formed. The slider 47A, or second slider is in threaded engagement with the threaded portion 48A, or a first threaded portion, and the slider 47B or a third slider is in threaded engagement with the threaded portion 48B or a second threaded portion. The threaded portions 48A and 48B are threaded in opposite directions to each other. In an example, the threaded portion 48A is a right-handed screw, while the threated portion 48B is a left-handed screw.

When by a control through the control dial 42, a control force is transmitted to the rotary shaft 45 and the rotary shaft 45 is rotated, the sliders 47A and 47B move in opposite directions relative to each other. When the rotary shaft 45 rotates in one of the opposite directions about the central axis thereof, for example, the sliders 47A and 47B separate from each other. When the rotary shaft 45 rotates in the other direction about the central axis thereof, on the other hand, the sliders 47A and 47B come closer to each other. As mentioned hereinbefore, by input of a control through the control dial 42, a control force is transmitted to the sliders 47A and 47B to move them.

The elongated member 25A is connected at a proximal end or opposite end thereof to the slider 47A, or second slider, and the elongated member 25B is connected at a proximal end or opposite end thereof to the slider 47B, or third slider. When the sliders 47A and 47B move in the opposite directions relative to each other, the elongated members 25A and 25B move in opposite directions relative to each other so that the end effector 5 is bent or curved. Here, the sliders 47A and 47B separate from each other, whereby the elongated member 25A moves toward the proximal end side, in other words, is pulled. As a consequence, the end effector 5 is bent or curved in one of bending directions or curving directions or to a side indicated by arrow B1. When the sliders 47A and 47B come closer to each other, on the other hand, the elongated member 25B moves toward the proximal end side, in other words, is pulled. As a consequence, the end effector 5 is bent or curved in the other bending direction or curving direction or to a side indicated by arrow B2.

In an example, the control dial 42, rotary shaft 45 and sliders 47A and 47B are attached to the housing 3. Even when the rotary knob 13 is rotated, the control dial 42, rotary shaft 45 and sliders 47A and 47B do not rotate about the longitudinal axis C. In another example, a rotary base (not illustrated) is additionally disposed in the treatment instrument 1. The rotary base is rotatable together with the sheath 2, end effector 5 and drive shaft 22 about the longitudinal axis C relative to the housing 3. The control dial 42, rotary shaft 45 and sliders 47A and 47B are attached to the rotary base. In this case, when the rotary knob 13 is rotated, the control dial 42, rotary shaft 45 and sliders 47A and 47B rotate together with the sheath 2, end effector 5 and drive shaft 22 about the longitudinal axis C relative to the housing 3.

FIGS. 3 and 4 illustrate the internal configuration of the housing 3 in a state in which the end effector 5 is neither bent nor curved with respect to the sheath 2 or the longitudinal axis C, in other words, in a neutral state that the end effector 5 is disposed extending straight relative to the sheath 2. Further, FIGS. 5 and 6 illustrate the internal configuration of the housing 3 in the state in which the end effector 5 is bent or curved with respect to the sheath 2 in the one bending direction or curving direction or to the side indicated by arrow B1. Furthermore, FIGS. 7 and 8 illustrate the internal configuration of the housing 3 in the state in which concerning the bending direction or curving direction, the end effector 5 is bent to the side opposite to that in the state of FIGS. 5 and 6 or to the side indicated by arrow B2 relative to the sheath 2.

In this embodiment, a flange 51 is formed on an inner circumferential surface of the cylinder member 33, and the flange 51 extends radially inward. The flange 51 is formed, for example, integrally with the cylinder member 33, and is arranged on the proximal end side with respect to the sliders 47A and 47B. Further, cylindrical elastic members 52A and 52B such as coil springs are arranged inside the housing 3. The elastic member 52A, or a second elastic member is connected at an end or a distal end thereof to the slider 47A, or second slider, and the elastic member 52A can come into contact at an opposite end or a proximal end thereof with the flange 51. Therefore, the elastic member 52A is disposed extending between the slider 47A and the flange 51, and can apply an restoring force, i.e., second restoring force toward the proximal end side to the drive shaft 22 at the flange 51. On the other hand, the elastic member 52B, or a third elastic member is connected at an end or a distal end thereof to the slider 47B, or third slider, and the elastic member 52B can come into contact at an opposite end or a proximal end thereof with the flange 51. Therefore, the elastic member 52B is disposed extending between the slider 47B and the flange 51, and can apply an restoring force or third restoring force toward the proximal end side to the drive shaft 22 at the flange 51. The elastic members 52A and 52B may preferably have the same elastic constants relative to each other.

The occurrence or non-occurrence of contact of the elastic member 52A, or second elastic member to the flange 51 and the amount of compression of the elastic member 52A from the natural length change corresponding to the position of the slider 47A, or second slider. Therefore, corresponding to the state of bending or the state of curving, such as the angle of bending or the angle of curving, of the end effector 5 with respect to the sheath 2, the occurrence or non-occurrence of contact of the elastic member 52A to the flange 51 and the amount of compression of the elastic member 52A change, and the restoring force or second restoring force to be applied from the elastic member 52A toward the proximal end side to the drive shaft 22 also changes. Similarly, the occurrence or non-occurrence of contact of the elastic member 52B, or third elastic member to the flange 51 and the amount of compression of the elastic member 52B from the natural length also change corresponding to the position of the slider 47B, or third slider. Therefore, corresponding to the state of bending or the state of curving, such as the angle of bending or the angle of curving, of the end effector 5 with respect to the sheath 2, the occurrence or non-occurrence of contact of the elastic member 52B to the flange 51 and the amount of compression of the elastic member 52B change, and the restoring force or third restoring force to be applied toward the proximal end side from the elastic member 52B to the drive shaft 22 also changes.

In the neutral state that the end effector 5 is not bent, the elastic member 52A, or second elastic member, as illustrated in FIG. 4, does not come into contact with the flange 51 of the drive shaft 22 or in the state of the natural length, comes into contact with the flange 51 when the drive shaft 22 moves toward the proximal end side to a state that the treatment target is compressed to a certain extent. In the neutral state, the restoring force or second restoring force is hence not applied from the elastic member 52A to the drive shaft 22 while the treatment target is grasped between the clamping members 17 and 18. Also, in the neutral state, the elastic member 52B, or third elastic member does not come into contact with the flange 51 of the drive shaft 22 or in the state of the natural length, comes into contact with the flange 51 when the drive shaft 22 moves toward the proximal end side to a state that the treatment target is compressed to a certain extent. In the neutral state, the restoring force or third restoring force is hence not applied from the elastic member 52B to the drive shaft 22 while the treatment target is grasped between the clamping members 17 and 18. In the neutral state, the resultant force of the restoring force or second restoring force from the elastic member 52A and the restoring force or third restoring force from the elastic member 52B therefore remains zero while the treatment target is grasped between the clamping members 17 and 18.

In a first bent state or first curved state in which the end effector 5 is bent or curved in the one bending direction or curving direction or to the side indicated by arrow B1, on the other hand, the slider 47A is located on the proximal end side compared with that in the neutral state as illustrated in FIG. 6. In the first bent state, the elastic member 52A, or second elastic member therefore comes into contact with the flange 51 in a state, in which the elastic member 52A, or second elastic member has been compressed from the natural length, even when the drive shaft 22 moves toward the proximal end side to a state that the treatment target is compressed to a certain extent. In the first bent state, the restoring force or second restoring force is hence applied from the elastic member 52A to the drive shaft 22 while the treatment target is grasped between the clamping members 17 and 18. Also, in the first bent state, the slider 47B is located on the distal end side compared with that in the neutral state. In the first bent state, the restoring force or third restoring force, as in the neutral state, is hence not applied either from the elastic member 52B to the drive shaft 22 while the treatment target is grasped between the clamping members 17 and 18.

As mentioned hereinbefore, the restoring force is applied from the elastic member 52A to the drive shaft 22 in the first bent state while the treatment target is grasped between the clamping members 17 and 18. In the first bent state, the resultant force of the restoring force or second restoring force to be applied from the elastic member 52A to the drive shaft 22 and the restoring force or third restoring force to be applied from the elastic member 52B to the drive shaft 22 therefore is greater than that in the neutral state while the treatment target is grasped between the clamping members 17 and 18. Also, in the first bent state or first curved state, the greater the angle of bending or the angle of curving of the end effector 5, on the more distal end side the position of the slider 47A. Accordingly, in the first bent state, the greater the angle of bending of the end effector 5, the greater the amount of compression of the elastic member 52A, or second elastic member from the natural length, and the greater the restoring force or second restoring force to be applied from the elastic member 52A to the drive shaft 22 while the treatment target is grasped between the clamping members 17 and 18. Therefore, in the first bent state, the greater the angle of bending, the greater the resultant force of the restoring force or second restoring force to be applied from the elastic member 52A to the drive shaft 22 and the restoring force or third restoring force to be applied from the elastic member 52B to the drive shaft 22 while the treatment target is grasped between the clamping members 17 and 18.

In a second bent state or second curved state in which the end effector 5 is bent or curved to a side opposite to the side in the state of FIG. 6 or to the side indicated by arrow B2, on the other hand, the slider 47B is located on the distal end side compared with that in the neutral state as illustrated in FIG. 8. In the second bent state, the elastic member 52B, or third elastic member therefore comes into contact with the flange 51 in a state, in which the elastic member 52B, or third elastic member has been compressed from the natural length, even when the drive shaft 22 moves toward the proximal end side to a state that the treatment target is compressed to a certain extent. In the second bent state, the restoring force or third restoring force is hence applied from the elastic member 52B to the drive shaft 22 while the treatment target is grasped between the clamping members 17 and 18. Also, in the second bent state, the slider 47A is located on the distal end side compared with that in the neutral state. In the second bent state, the restoring force or second restoring force, as in the neutral state, is hence not applied either from the elastic member 52A to the drive shaft 22 while the treatment target is grasped between the clamping members 17 and 18.

As mentioned hereinbefore, the restoring force is applied from the elastic member 52B to the drive shaft 22 in the second bent state while the treatment target is grasped between the clamping members 17 and 18. In the second bent state, the resultant force of the restoring force or second restoring force to be applied from the elastic member 52A to the drive shaft 22 and the restoring force or third restoring force to be applied from the elastic member 52B to the drive shaft 22 therefore is greater than that in the neutral state while the treatment target is grasped between the clamping members 17 and 18. Also, in the second bent state or second curved state, the greater the angle of bending or the angle of curving of the end effector 5, on the more distal end side the position of the slider 47B. Accordingly, in the second bent state, the greater the angle of bending of the end effector 5, the greater the amount of compression of the elastic member 52B, or third elastic member from the natural length, and the greater the restoring force or third restoring force to be applied from the elastic member 52B to the drive shaft 22, while the treatment target is grasped between the clamping members 17 and 18. Therefore, in the second bent state, the greater the angle of bending, the greater the resultant force of the restoring force or second restoring force to be applied from the elastic member 52A to the drive shaft 22 and the restoring force or third restoring force to be applied from the elastic member 52B to the drive shaft 22 while the treatment target is grasped between the clamping members 17 and 18.

When the elastic members 52A and 52B have the same elastic constants, changes in the restoring force from the elastic member 52A to the drive shaft according to changes in the angle of bending in the first bent state present a similar tendency as changes in the restoring force from the elastic member 52A to the drive shaft according to changes in the angle of bending in the second bent state.

A description will next be made regarding operation and advantageous effects of the treatment instrument 1 of this embodiment. Upon treatment of a treatment target such as a body tissue with the treatment instrument 1, an operator holds the housing 3 by a hand, and inserts the end effector 5 into a body cavity such as the abdominal cavity. The operator then controls the position and posture of the end effector 5 in the body cavity by rotating the sheath 2 and end effector 5 about the longitudinal axis C through rotation of the rotary knob 13 or by bending the end effector 5 with respect to the sheath 2 through a control at the control dial 42. When the position and posture of the end effector 5 are controlled into states that the treatment target is placed between the clamping members 17 and 18, the grip handle 11 is closed toward the grip 7, whereby the clamping members 17 and 18 are closed relative to each other. Here, the grip handle 11 is closed toward the grip, for example, until the grip handle 11 comes into contact with the stopper 9. As a consequence, an axial force is applied to the drive shaft 22 and end effector 5 so that the treatment target is grasped between the clamping members 17 and 18. When an operation is inputted through the operation button 21 in the state that the treatment target is grasped, electrical energy is supplied to the treatment instrument 1 so that treatment energy such as high-frequency current is applied to or a staple is driven through the treatment target grasped as mentioned hereinbefore.

Now, it is required in a treatment to control the amount of grasping force between the clamping members 17 and 18 to a level suited for the treatment corresponding to the state of bending or the state of curving of the end effector 5. For example, it is required in a treatment to make uniform or substantially uniform the amount of grasping force between the clamping members 17 and 18 at any angle of bending or curving of the end effector 5 if other conditions such as the size of the treatment target are the same. If such other conditions are the same, the amount of grasping force is hence required to be the same or substantially the same both in the neutral state that the end effector 5 is not bent and in the state that the end effector 5 is bent.

Now, the amount of grasping force between the clamping members 17 and 18 changes corresponding to the axial force applied toward the proximal end side from the drive shaft 22 to the end effector 5. The greater the axial force transmitted from the drive shaft 22 to the end effector 5, the greater the amount of grasping force. When the end effector 5 is bent or curved with respect to the sheath 2, the distal end portion of the drive shaft 22 is bent to curved as mentioned hereinbefore. If the distal end portion of the drive shaft 22 is bent or curved, a portion of the drive shaft 22, the portion being on the proximal end side with respect to the link mechanism 23, is located off the longitudinal axis C. If the distal end portion of the drive shaft 22 is bent or curved, the axial force to be transmitted through the drive shaft 22 therefore is decomposed at the link mechanism 23. Component forces occurred through decomposition at the link mechanism 23 are then transmitted as an axial force to the end effector 5 through the distal end portion of the drive shaft 22. When the drive shaft 22 is bent or curved at the distal end portion thereof, the axial force to be transmitted from the drive shaft 22 to the end effector 5 therefore decreases compared with that in the neutral state that the drive shaft 22 is straight over the entirety thereof. In addition, when the drive shaft 22 is bent or curved at the distal end portion thereof, a loss of the axial force of the drive shaft 22 occurs by friction or the like. The greater the bent angle of bending of the end effector 5, the greater the decrease of the axial force of the drive shaft 22 at the bent portion or curved portion of the drive shaft 22, in other words, the effect of the component forces. If other conditions are the same, the greater the decrease of the axial force of the drive shaft 22 at the bent portion thereof by the effect of the component force, the smaller the amount of grasping force.

In this embodiment, the axial force to be transmitted to the drive shaft 22, which affects the amount of grasping force, changes corresponding to the restoring forces transmitted from the respective elastic members 52A and 52B to the drive shaft 22 in addition to the restoring force transmitted from the elastic member 36 to the drive shaft 22. Described specifically, if other conditions are the same, the greater the resultant force of the restoring force or first restoring force applied from the elastic member 36 to the drive shaft 22, the restoring force or second restoring force applied from the elastic member 52A to the drive shaft 22 and the restoring force or the third restoring force applied from the elastic member 52B to the drive shaft 22, the greater the axial force from the drive shaft 22 to the end effector 5, in other words, the amount of grasping force between the clamping members 17 and 18.

In this embodiment, an restoring force is applied from the elastic member 52A to the drive shaft 22 in the first bent state or first curved state, but no restoring force is applied from the elastic member 52A to the drive shaft 22, as mentioned hereinbefore. If other conditions such as the size of the treatment target and the like are the same, the resultant force of the restoring forces from the elastic members 36, 52A, and 52B in the first bent state therefore is greater compared with that in the neutral state. In the first bent state, the effect on the amount of grasping force by the decrease of the axial force due to the bending of the drive shaft 22 therefore is cancelled by the effect of the restoring force or second restoring force from the elastic member 52A on the amount of grasping force. In other words, in the first bent state, the axial force of the drive shaft 22 at a position thereof closer to the end effector 5 than the bent portion decreases compared with the axial force of the drive shaft 22 at a position farther from the end effector 5 than the bent portion, but the restoring force or second restoring force from the elastic member 52A is greater compared with that in the neutral state. If other conditions are the same as in a case where the size of the treatment target is the same and the restoring force or first restoring force from the elastic member 36 is the same, the axial force of the drive shaft 22, which is to be applied to the end effector 5, in other words, the amount of grasping force therefore is the same or substantially the same in both the first bent state and the neutral state. In the first bent state, the axial force at a position of the drive shaft 22 on the proximal end side with respect to the link mechanism 23 is great compared with that in the neutral state. In the first bent state, the axial force to be applied to the end effector 5 therefore is the same or substantially the same as that in the neutral state even if the axial force at a position of the drive shaft 22 on the distal end side with respect to the link mechanism 23 decreases by the effect of a component force compared with that at a position of the drive shaft 22 on the proximal end side with respect to the link mechanism 23.

In the first bent state, the greater the angle of bending or angle of curving, the greater the restoring force from the elastic member 52A to the drive shaft 22. In the first bent state, even if the angle of bending or angle of curving of the end effector increases and the amount of decrease of the axial force of the drive shaft 22 at the bent portion thereof increases, the effect on the amount of grasping force by the decrease of the axial force of the drive shaft 22 at the bent portion thereof therefore is cancelled by the effect of the restoring force or second restoring force from the elastic member 52A on the amount of grasping force. Therefore, in the first bent state, the greater the amount of decrease of the axial force of the drive shaft 22 at the bent portion thereof, the greater the restoring force or second restoring force from the elastic member 52A. In the first bent state, if other conditions are the same, the axial force of the drive shaft 22, which is to be applied to the end effector 5, in other words, the amount of grasping force remains uniform or substantially uniform at any angle of bending.

In the second bent state, on the other hand, the effect on the amount of grasping force by the decrease of the axial force of the drive shaft 22 at the bent portion thereof is cancelled by the effect of the restoring force or third restoring force from the elastic member 52B on the amount of grasping force. Therefore, in the second bent state, the amount of decrease of the axial force of the drive shaft 22 at the bent portion thereof, the amount of decrease of the axial force of the drive shaft 22 at the bent portion thereof is great compared with that in the neutral state, but the restoring force or third restoring force from the elastic member 52B is great compared with that in the neutral state. If other conditions are the same, the axial force of the drive shaft 22, which is to be applied to the end effector 5, in other words, the amount of grasping force is the same or substantially the same in both the second bent state and the neutral state.

Also, in the second bent state, the greater the angle of bending of the end effector 5, in other words, the greater the amount of decrease of the axial force of the drive shaft 22 at the bent portion thereof, the greater the restoring force or third restoring force from the elastic member 52B. In the second bent state, if other conditions are the same, the axial force of the drive shaft 22, which is to be applied to the end effector 5, in other words, the amount of grasping force remains uniform or substantially uniform at any angle of bending.

Further, setting of the elastic members 52A and 52B at the same elastic constants makes the same or substantially the same the axial force of the drive shaft 22, which is to be applied to the end effector 5, in other words, the amount of grasping force in both the first bent state and the second bent state in which the end effector 5 is bent to the side opposite to that in the first bent state.

In this embodiment, owing to the disposition of the elastic members 52A and 52B, the axial force of the drive shaft 22, in other words, the amount of grasping force between the clamping members 17 and 18 remains uniform or substantially uniform at any angle of bending of the end effector 5 as mentioned hereinbefore. Therefore, corresponding to the state of bending or the state of curving of the end effector, the restoring forces from the respective elastic members 52A and 52B to the drive shaft 22 change so that the grasping force is controlled to a level suited for the treatment. Further, through control of the restoring forces from the elastic members 52A and 52B, for example, by adjustment of their elastic constants or the like in view of the effect of a loss due to friction or the like, the axial force of the drive shaft 22 can be made greater at a position thereof on the distal end side with respect to the link mechanism 23 in the first bent state and the second bent state, respectively than that in the neutral state.

Modifications

In the embodiment and the like mentioned hereinbefore, the clamping members 17 and 18 close relative to each other when the drive shaft 22 moves toward the proximal end side. However, the disclosed technology is not limited to such a configuration. In a modification illustrated in FIGS. 9 and 10, the clamping members 17 and 18 close relative to each other when the drive shaft 22 moves toward the distal end side. In this modification, the cylinder member 33 and slider 35 are disposed on a side opposite to the operating-force applied portion 12 with respect to the fulcrum pin 26 or the pivot P1. Therefore, the engagement portion of the grip handle 11 with the groove 41 of the slider 35 is located on a side opposite to the operating-force applied portion 12 with respect to the fulcrum pin 26 or the pivot P1. In this modification, the slider or first slider 35 is disposed on the proximal end side with respect to a flange 38 of the drive shaft 22. Further, a stopper 37 is disposed on the proximal end side with respect to the slider 35, whereby movement of the slider 35 beyond the stopper 37 to a region on the proximal end side is restricted.

In this modification, the elastic member 36, or first elastic member is in contact or connected at the one end or proximal end thereof with or to a flange 38 of the drive shaft 22. On the other hand, the elastic member 36 is in contact or connected at the opposite end or proximal end thereof with or to the slider 35. In this modification, when the grip handle 11 is closed toward the grip 7 with a treatment target placed between the clamping members 17 and 18, the drive shaft 22 moves together with the slider 35 and elastic member 36 toward the proximal end side relative to the sheath 2 so that the clamping members 17 and 18 close relative to each other. When the grasped treatment target is compressed to a certain extent, the movement of the drive shaft 22 toward the distal end side stops. When the grip handle 11 is closed toward the grip 7 in this state until the grip handle 11 comes into contact with the stopper 9, the slider 35, or first slider moves toward the distal end side relative to the drive shaft 22. As a consequence, the elastic member 36, or first elastic member is compressed, leading to an increase of the restoring force applied toward the distal end side from the elastic member 36 to the drive shaft 22. The increase of the restoring force from the elastic member 36 to the drive shaft 22 then leads to an increase of the axial force applied toward the distal end side from the drive shaft 22 to the end effector 5, and hence to an increase of the amount of grasping force on the treatment target between the clamping members 17 and 18.

In this modification, an elastic member 52A is connected at an end or proximal end thereof to a slider 47A, and can come into contact at an opposite end or distal end thereof with the transmission member 32. On the other hand, an elastic member 52B is connected at an end or proximal end thereof to a slider 47B, and can come into contact at an opposite end or distal end thereof with the transmission member 32. In this modification, the elastic members 52A and 52B can hence each apply an restoring force toward the distal end side to the transmission member 32 of the drive shaft 22. In this modification, the slider 47A is also located on the proximal end side with respect to the slider 47B.

In the neutral state that the end effector 5 is disposed extending straight relative to the sheath 2, the elastic members 52A and 52B each do not come into contact with the transmission member 32 of the drive shaft 22 or in the state of the natural length, each come into contact with the transmission member 32 even when the drive shaft 22 moves toward the distal end side to a state that the treatment target is compressed to a certain extent. As in the embodiment and the like mentioned hereinbefore, no restoring force is hence applied from the elastic members 52A and 52B to the drive shaft 22 in the neutral state while the treatment target is grasped between the clamping members 17 and 18.

Figure 9:
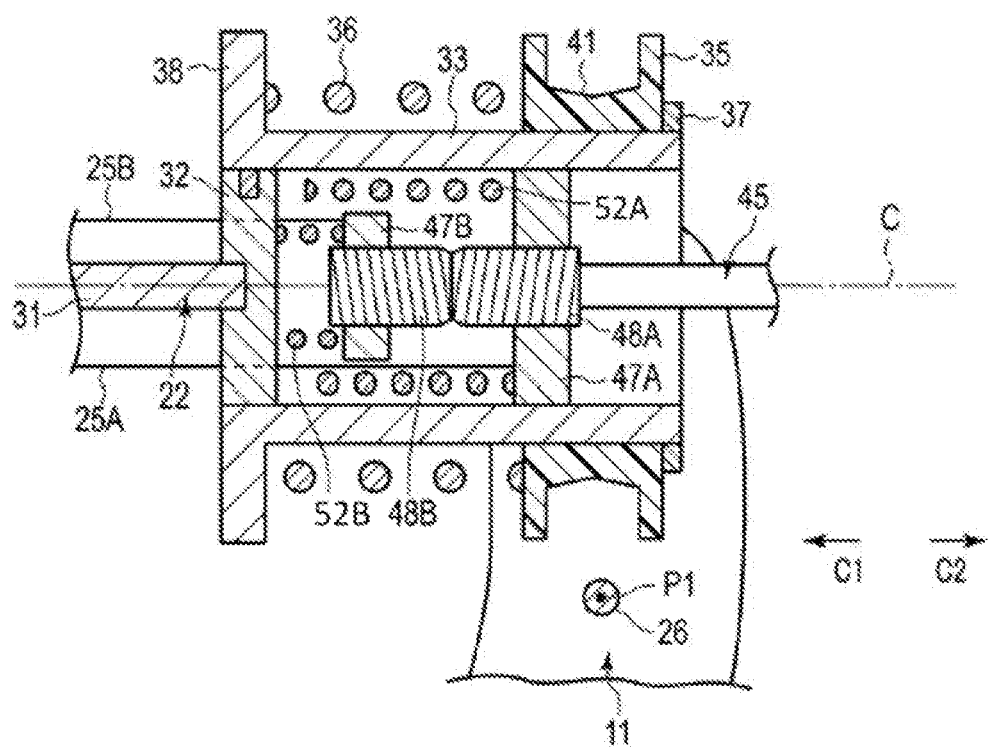
FIG. 9 is a schematic view illustrating an internal configuration of a housing in a modification of the first embodiment, with end effector being in a state in which the end effector is bent toward one side in bending direction and clamping members being in a state in which the clamping members are widely opened relative to one another.
Figure 10:
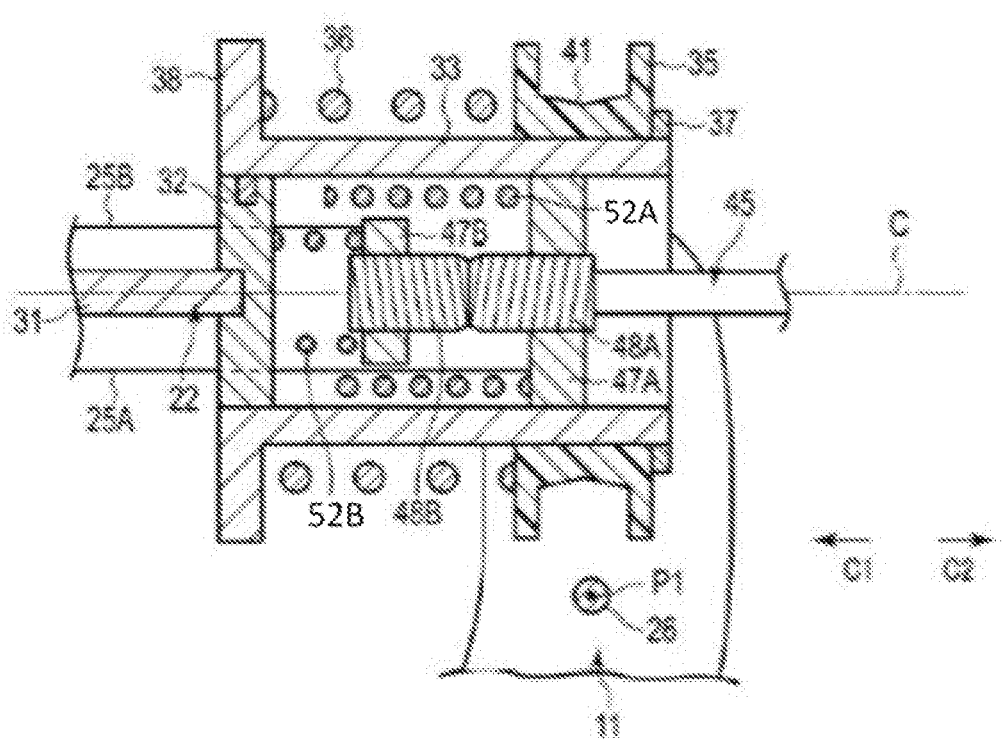
FIG. 10 is a schematic view illustrating the internal configuration of the housing in the modification of the first embodiment, with the end effector being in the state in which the end effector is bent toward the one side in bending direction and the drive shaft being in a state in which movement of the drive shaft toward a proximal end side has stopped.

FIGS. 9 and 10 illustrate the internal configuration of the housing 3 in a first bent state in which the elongated member 25A has moved toward the proximal end side from the neutral state and the end effector has been bent to one of bending directions or curving directions. More specifically, FIG. 9 illustrates the internal configuration of the housing 3 in a state in which the clamping members 17 and 18 are most opened relative to each other, and FIG. 10 illustrates the internal configuration of the housing 3 in a state in which the grasped treatment target has been compressed to a certain extent and the movement of the drive shaft 22 toward the distal end side has stopped.

In this modification, in the first bent state or first curved state, the slider 47B, or second slider is located on the distal end side compared with that in the neutral state as illustrated in FIGS. 9 and 10. In the first bent state, the elastic member 52B, or second elastic member therefore comes into contact with the transmission member 32 in a state, in which the elastic member 52B, or second elastic member has been compressed from the natural length, even when the drive shaft 22 moves toward the distal end side to a state that the treatment target is compressed to a certain extent. In the first bent state, an restoring force or second restoring force is hence applied from the elastic member 52B to the drive shaft 22 while the treatment target is grasped between the clamping members 17 and 18. In the first bent state, an restoring force or third restoring force, as in the neutral state, is not applied either from the elastic member 52A, or third elastic member to the drive shaft 22 while the treatment target is grasped between the clamping members 17 and 18.

In the first bent state, the resultant force of the restoring force or third restoring force to be applied from the elastic member 52A to the drive shaft 22 and the restoring force or second restoring force to be applied from the elastic member 52B to the drive shaft 22 therefore is greater than that in the neutral state while the treatment target is grasped between the clamping members 17 and 18. In the first bent state or first curved state, the greater the angle of bending or the angle of curving of the end effector 5, on the more distal end side the position of the slider 47B. Accordingly, in the first bent state, the greater the angle of bending of the end effector 5, the greater the amount of compression of the elastic member 52B, or second elastic member from the natural length, and the greater the restoring force or second restoring force to be applied from the elastic member 52B to the drive shaft 22 while the treatment target is grasped between the clamping members 17 and 18. Therefore, in the first bent state, the greater the angle of bending, the greater the resultant force of the restoring force or third restoring force to be applied from the elastic member 52A to the drive shaft 22 and the restoring force or second restoring force to be applied from the elastic member 52B to the drive shaft 22 while the treatment target is grasped between the clamping members 17 and 18.

In a second bent state or second curved state in which the end effector 5 is bent or curved to a side opposite to the side in the state of FIG. 10 or to the side indicated by arrow B2, on the other hand, the slider 47A, or third slider is located on the distal end side compared with that in the neutral state. In the second bent state, the elastic member 52A, or third elastic member therefore comes into contact with the transmission member 32 in a state, in which the elastic member 52A, or third elastic member has been compressed from the natural length, even when the drive shaft 22 moves toward the distal end side to a state that the treatment target is compressed to a certain extent. In the second bent state, the restoring force or third restoring force is hence applied from the elastic member 52A to the drive shaft 22 while the treatment target is grasped between the clamping members 17 and 18. In the second bent state, the restoring force or second restoring force, as in the neutral state, is not applied either from the elastic member 52B, or second elastic member to the drive shaft 22 while the treatment target is grasped between the clamping members 17 and 18.

In this modification, the resultant force of the restoring force or third restoring force to be applied from the elastic member 52A to the drive shaft 22 and the restoring force or second restoring force to be applied from the elastic member 52B to the drive shaft 22 therefore is also greater in the second bent state than that in the neutral state while the treatment target is grasped between the clamping members 17 and 18. In the second bent state or second curved state, the greater the angle of bending or the angle of curving of the end effector 5, on the more distal end side the position of the slider 47A. Accordingly, in the second bent state, the greater the angle of bending of the end effector 5, the greater the amount of compression of the elastic member 52A, or third elastic member from the natural length, and the greater the restoring force or third restoring force to be applied from the elastic member 52A to the drive shaft 22, while the treatment target is grasped between the clamping members 17 and 18. Therefore, in the second bent state, the greater the angle of bending, the greater the resultant force of the restoring force or third restoring force to be applied from the elastic member 52A to the drive shaft 22 and the restoring force or second restoring force to be applied from the elastic member 52B to the drive shaft 22 while the treatment target is grasped between the clamping members 17 and 18.

Owing to the configuration as mentioned hereinbefore, in this modification, the effect on the amount of grasping force by the decrease of the axial force of the drive shaft 22 at the bent portion thereof therefore is cancelled by the effect of the restoring force or second restoring force from the elastic member 52B on the amount of grasping force in the first bent state. In other words, in the first bent state, the axial force of the drive shaft 22 at the bent portion thereof decreases compared with that in the neutral state, but the restoring force or second restoring force from the elastic member 52B is greater compared with that in the neutral state. If other conditions are the same as in a case where the size of the treatment target is the same and the restoring force or first restoring force from the elastic member 36 is the same, the axial force of the drive shaft 22, which is to be applied to the end effector 5, in other words, the amount of grasping force therefore is the same or substantially the same in both the first bent state and the neutral state.

Also, in this modification, even if the angle of bending or angle of curving of the end effector increases and the amount of decrease of the axial force of the drive shaft 22 at the bent portion thereof increases in the first bent state, the effect on the amount of grasping force by the decrease of the axial force of the drive shaft 22 at the bent portion thereof therefore is cancelled by the effect of the restoring force or second restoring force from the elastic member 52B on the amount of grasping force. Therefore, in the first bent state, the greater the amount of decrease of the axial force of the drive shaft 22 at the bent portion thereof, the greater the restoring force or second restoring force from the elastic member 52B. In the first bent state, if other conditions are the same, the axial force of the drive shaft 22, which is to be applied to the end effector 5, in other words, the amount of grasping force hence remains uniform or substantially uniform at any angle of bending.

In this modification, the effect on the amount of grasping force by the decrease of the axial force of the drive shaft 22 at the bent portion thereof is cancelled by the effect of the restoring force or third restoring force from the elastic member 52A on the amount of grasping force in the second bent state. Therefore, in the second bent state, the amount of decrease of the axial force of the drive shaft 22 at the bent portion thereof is great compared with that in the neutral state, but the restoring force or third restoring force from the elastic member 52A is great compared with that in the neutral state. If other conditions are the same, the axial force of the drive shaft 22, which is to be applied to the end effector 5, in other words, the amount of grasping force is the same or substantially the same in both the second bent state and the neutral state.

In this modification, even if in the second bent state, the angle of bending or the angle of curving of the end effector increases and the amount of decrease of the axial force of the drive shaft 22 at the bent portion thereof increases, the effect on the amount of grasping force by the decrease of the axial force of the drive shaft 22 at the bent portion thereof is cancelled by the effect of the restoring force or third restoring force from the elastic member 52A on the amount of grasping force. In other words, in the second bent state, the greater the amount of decrease of the axial force of the drive shaft 22 at the bent portion thereof, the greater the restoring force or third restoring force from the elastic member 52A. In the second bent state, if other conditions are the same, the axial force of the drive shaft 22, which is to be applied to the end effector 5, in other words, the amount of grasping force therefore remains uniform or substantially uniform at any angle of bending.

As mentioned hereinbefore, owing to the disposition of the elastic members 52A and 52B, the axial force of the drive shaft 22, in other words, the amount of grasping force between the clamping members 17 and 18 also remains uniform or substantially uniform at any angle of bending of the end effector 5 in this modification as in the embodiment and the like mentioned hereinbefore. Therefore, corresponding to the state of bending or the state of curving of the end effector, the restoring forces from the respective elastic members 52A and 52B to the drive shaft 22 change so that the grasping force is controlled to a level suited for the treatment.

The configuration of attachment of a control member such as the control dial 42 to the housing and the configuration for the transmission of a control force from the control member (42) to the sliders 47A and 47B should not be limited to the configurations mentioned hereinbefore. In a modification, for example, the control dial 42 is rotatable relative to the housing 3 about the axis P2 of rotation that is substantially parallel to the longitudinal axis C. In another modification, a control force is transmitted from the control dial 42 to the rotary shaft 45 via one or more gears or the like.

In a modification, the end effector 5 can be bent or curved to only one side from the neutral state that the end effector is straight. In this case, the treatment instrument 1 includes only the elongated member 25A. When the elongated member 25A moves in an axial direction thereof, the end effector 5 is bent. In this modification, when the slider 47A, or second slider moves, and the restoring force or second restoring force from the elastic member 52A, or second elastic member to the drive shaft 22 also changes concurrently with the movement of the elongated member 25A. The restoring force from the elastic member 52A to the drive shaft 22 therefore also changes in this modification when the end effector 5 is bent from the neutral state that the end effector 5 is straight.

In the embodiment and the like mentioned hereinbefore, when the restoring forces from the respective elastic members 52A and 52B to the drive shaft 22 change corresponding to the state of bending or the state of curving of the end effector, the axial force of the drive shaft 22, which is to be applied to the end effector, in other words, the amount of grasping force between the clamping members 17 and 18 remains uniform or substantially uniform at any angle of bending of the end effector 5 if other conditions are the same. However, the disclosed technology should not be limited to such a configuration. In a modification, the restoring forces from the respective elastic members 52A and 52B to the drive shaft 22 change, for example, corresponding to the state of bending or the state of curving of the end effector. If other conditions are the same, owing to this configuration, the axial force of the drive shaft 22, in other words, the amount of grasping force between the clamping member 17 and 18 increases as the angle of bending of the end effector 5 becomes greater.

In the embodiment and the like mentioned hereinbefore, the end effector 5 with the pair of clamping members 17 and 18 included therein is attached to the sheath 2 so that the end effector 5 can be bent or curved. When the drive shaft 22 moves relative to the sheath 2, the pair of clamping members 17 and 18 open or close relative to each other. When the elongated members 25A and 25B move relative to the sheath 2, the end effector 5 is bent or curved with respect to the sheath 2. When the first slider 35 moves relative to the drive shaft 22, the first restoring force from the first elastic member 36 to the drive shaft 22 changes. Further, when the second sliders 47A and 47B move, the second restoring force from the second elastic members 52A and 52B to the drive shaft 22 changes concurrently with the movement of the elongated members 25A and 25B.

The disclosed technology is not limited to the embodiment and modifications described hereinbefore, and various modifications are possible in practice within a scope not departing from the spirit of the present invention. Further, the individual embodiment and modifications may be practiced in combination as much as possible as needed, and in such cases, combined advantageous effects can be brought about. Furthermore, inventions of various levels are included in the embodiment and modifications described hereinbefore, and a variety of inventions can be derived by appropriate combinations of the plural features disclosed herein.

In sum, one aspect of the disclosed technology is directed to a treatment instrument comprises an end effector having a pair of clamping members configured to pivot with respect to one another so as to be in an open or close position. A sheath is attached to the end effector along a longitudinal axis so that the end effector can be bent or curved. A drive shaft is connected to the end effector so as to guide the end effector to open or close the pair of clamping members relative to one another when moved in a longitudinal direction relative to the sheath. An elongated member is connected to the end effector and is configured to make the end effector bend or curve with respect to the sheath when moved in the longitudinal direction relative to the sheath. A first member is configured to produce a first force sufficient to open or close the pair of clamping members and to apply the first force to the drive shaft. A second member is configured to produce a second force that corresponds to a degree of bending or curving of the end effector and to apply the second force to the drive shaft.

The second force applied from the second member to the drive shaft is greater when the end effector is bent or curved with respect to the sheath than when the end effector is in a neutral state, in which the end effector is positioned straight relative to the sheath. The first member is a first elastic member configured to apply a first restoring force to the drive shaft. The second member is a second elastic member configured to apply a second restoring force to the drive shaft. The treatment instrument further includes a first slider configured to change magnitude of the first restoring force, which is to be applied from the first elastic member to the drive shaft, when moved in the longitudinal direction relative to the drive shaft. A second slider is configured to move the elongated member and concurrently with resulting movement of the elongated member, to change magnitude of the second restoring force, which is to be applied from the second elastic member to the drive shaft, when moved in the longitudinal direction relative to the drive shaft. The treatment instrument further comprises a third elastic member configured to enable application of a third restoring force to the drive shaft.

A third slider is configured to move in the longitudinal direction in conjunction with the movement of the second slider and concurrently with the movement of the elongated member, to change magnitude of the third restoring force to be applied from the third elastic member to the drive shaft. A resultant force of the second restoring force and the third restoring force to be applied to the drive shaft is greater when the end effector is bent or curved with respect to the sheath than when the end effector is in a neutral state, in which the end effector is positioned straight relative to the sheath. The treatment instrument further comprises a rotary shaft used to carry the respective second and third sliders mounted thereon and is configured to move the respective second and third sliders in opposite directions, when rotated. The rotary shaft further includes a first threaded portion carrying the second slider thereon in threaded engagement therewith, and a second threaded portion carrying the third slider thereon in treaded engagement therewith and threaded in an opposite direction to the first threaded portion. The treatment instrument further comprises a control member configured to transmit a control force to the second slider to move the second slider when rotated by the control force. The drive shaft includes one of a link mechanism, a leaf spring, and/or a rope at a position thereof where the drive shaft passes between the end effector and the sheath.

Another aspect of the disclosed technology is directed to a treatment instrument comprises a housing and a sheath is attached to the housing along a longitudinal axis. An end effector is configured to be attached to the sheath so as to be bend or curved with respect to the sheath. The end effector includes a pair of clamping members configured to pivot with respect to one another so as to be in an open or close position. A drive shaft is configured to be disposed inside the sheath and is connected to the end effector so as to guide the end effector to open or close the pair of clamping members relative to one another when moved in a longitudinal direction relative to the sheath. An elongated member is connected to the end effector and is configured to make the end effector bend or curve with respect to the sheath when moved in the longitudinal direction relative to the sheath. A first member is configured to produce a first force sufficient to open or close the pair of clamping members and to apply the first force to the drive shaft. A second member is configured to produce a second force that corresponds to a degree of bending or curving of the end effector and to apply the second force to the drive shaft.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment instrument comprising:
    an end effector including a pair of clamping members configured to pivot with respect to one another so as to be in an open or close position,
    a sheath being attached to the end effector along a longitudinal axis so that the end effector can be bent or curved, a drive shaft being connected to the end effector so as to guide the end effector to open or close the pair of clamping members relative to one another when moved in a longitudinal direction relative to the sheath, an elongated member being connected to the end effector and being configured to make the end effector bend or curve with respect to the sheath when moved in the longitudinal direction relative to the sheath, a first elastic member being configured to apply a first restoring force to the drive shaft, a first slider configured to change magnitude of the first restoring force, which is to be applied from the first elastic member to the drive shaft, when the first slider is moved in the longitudinal direction relative to the drive shaft in accordance with opening or closing of the pair of clamping members, a second elastic member being configured to apply a second restoring force to the drive shaft, and a second slider configured to move the elongated member and, concurrently with resulting movement of the elongated member, change magnitude of the second restoring force, which is to be applied from the second elastic member to the drive shaft, when the second slider is moved in the longitudinal direction relative to the drive shaft in accordance with bending or curving of the end effector.

2. The treatment instrument of claim 1, wherein
the second restoring force applied from the second elastic member to the drive shaft is greater when the end effector is bent or curved with respect to the sheath than when the end effector is in a neutral state, in which the end effector is positioned straight relative to the sheath.

3. The treatment instrument of claim 1 further comprising:
a third elastic member configured to apply a third restoring force to the drive shaft, and
a third slider configured to move in the longitudinal direction in conjunction with the movement of the second slider and concurrently with the movement of the elongated member, to change magnitude of the third restoring force to be applied from the third elastic member to the drive shaft.

4. The treatment instrument of claim 3, wherein
a resultant force of the second restoring force and the third restoring force is greater when the end effector is bent or curved with respect to the sheath than when the end effector is in a neutral state, in which the end effector is positioned straight relative to the sheath.

5. The treatment instrument of claim 3 further comprising:
a rotary shaft used to carry the respective second and third sliders mounted thereon and being configured to move the respective second and third sliders in opposite directions, when rotated.

6. The treatment instrument of claim 5, wherein
the rotary shaft further includes a first threaded portion carrying the second slider thereon in threaded engagement therewith, and a second threaded portion carrying the third slider thereon in treaded engagement therewith and threaded in an opposite direction to the first threaded portion.

7. The treatment instrument of claim 1 further comprising:
a control member configured to transmit a control force to the second slider to move the second slider when rotated by the control force.

8. The treatment instrument of claim 1, wherein
the drive shaft includes one of a link mechanism, a leaf spring, and/or a rope at a position thereof where the drive shaft passes between the end effector and the sheath.

9. A treatment instrument comprising:
a housing,
a sheath being attached to the housing along a longitudinal axis,
an end effector configured to be attached to the sheath so as to be bend or curved with respect to the sheath, the end effector including a pair of clamping members configured to pivot with respect to one another so as to be in an open or close position,
a drive shaft configured to be disposed inside the sheath and being connected to the end effector so as to guide the end effector to open or close the pair of clamping members relative to one another when moved in a longitudinal direction relative to the sheath,
an elongated member being connected to the end effector and being configured to make the end effector bend or curve with respect to the sheath when moved in the longitudinal direction relative to the sheath,
a first elastic member being configured to apply a first restoring force to the drive shaft,
a first slider configured to change magnitude of the first restoring force, which is to be applied from the first elastic member to the drive shaft, when the first slider is moved in the longitudinal direction relative to the drive shaft in accordance with opening or closing of the pair of clamping members,
a second elastic member being configured to apply a second restoring force to the drive shaft, and
a second slider configured to move the elongated member and, concurrently with resulting movement of the elongated member, change magnitude of the second restoring force, which is to be applied from the second elastic member to the drive shaft, when the second slider is moved in the longitudinal direction relative to the drive shaft in accordance with bending or curving of the end effector.

* * * * *